United States Patent
Broadhurst et al.

(10) Patent No.: US 6,265,446 B1
(45) Date of Patent: Jul. 24, 2001

(54) HYDRAZINE DERIVATIVES

(75) Inventors: Michael John Broadhurst, Royston; William Henry Johnson, Bodmin; Daryl Simon Walter, Knebworth, all of (GB)

(73) Assignee: Hoffmann-La Roche Inc.., Nutley, NJ (US)

( * ) Notice: Subject to any disclaimer, the term of this patent is extended or adjusted under 35 U.S.C. 154(b) by 0 days.

(21) Appl. No.: 09/444,861

(22) Filed: Nov. 22, 1999

(30) Foreign Application Priority Data

Nov. 27, 1998 (GB) .................................. 9826153

(51) Int. Cl.⁷ .................. A61K 31/18; A61K 31/63; A61K 31/5375; A61K 31/5377; A61K 31/4402
(52) U.S. Cl. ............... 514/605; 514/238.2; 514/357; 514/603; 514/604; 514/824; 514/863; 544/149; 544/160; 546/282.1; 546/332; 549/419; 556/419; 564/81
(58) Field of Search ................ 514/238.2, 357, 514/603, 604, 605, 824, 863; 544/149, 160; 546/282.1, 332; 549/419; 556/419; 564/81

(56) References Cited

U.S. PATENT DOCUMENTS

| | | | |
|---|---|---|---|
| 5,304,549 | 4/1994 | Broadhurst et al. | 514/80 |
| 5,399,589 | 3/1995 | Rentzea et al. | 514/615 |

FOREIGN PATENT DOCUMENTS

| | | |
|---|---|---|
| 198 29 229 | 1/1999 | (DE) . |
| 497 192 | 8/1992 | (EP) . |
| WO 97/37973 | 10/1997 | (WO) . |
| WO 98/11063 | 3/1998 | (WO) . |
| WO 99/01428 | 1/1999 | (WO) . |
| WO 99/40063 | 8/1999 | (WO) . |
| WO 00/00465 | 1/2000 | (WO) . |

OTHER PUBLICATIONS

Chemical Abstracts, vol. 104, No. 9, Abstract No. 61519p, Mar. 3, 1986.
Coffey, R. J. et al., Nature (1987) 328, pp. 817–820.
Karashima, T. et al., Dermatol. Sci. (1996) 12, pp. 246–254.
Olanrian A. et al., Arch. Dermatol. Res. (1995) 287, pp. 231–236.
Chemical Abstr., General Substances Index, vol. 11ᵗʰ Collective, 1982–1986, p. 14, 583 CS, Compound with RN 87362–025 which is 2–(phenylsulfonyl)hydrazide.
Chernyk et al., "Biologically Active Substances in Hydrazide Derivatives of Succinic Heterylamides", Khimiko–farmatsevticheskii Zhurnal, vol. 23, No. 7, pp. 825–828 (1989).
Kratasyuk et al., "The Effect of Succinic Acid Sulfoderivatives on Bacterial Luminescence", Prikl. Biokhim. Mikrobiol., vol. 27(1): 127–133 (1991).

*Primary Examiner*—Peter O'Sullivan
(74) *Attorney, Agent, or Firm*—George W. Johnston; William H. Epstein; Lewis J. Kreisler

(57) ABSTRACT

Hydrazine derivatives of the formula (I)

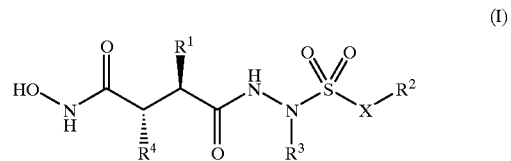

wherein $R^1$ represents lower alkyl, lower alkenyl, lower cycloalkyl, lower cycloalkyl-lower alkyl, aryl or aryl-lower alkyl, $R^2$ represents heterocyclyl or $NR^5R^6$, $R^3$ represents hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl, $R^4$ represents lower alkyl, lower alkenyl, lower cycloalkyl, lower cycloalkyl-lower alkyl or a grouping of the formula -Z-aryl, -Z-heterocyclyl or $—(CH_2)_n—$, $CH=CR^7R^8$, $R^5$ and $R^6$ each independently represent hydrogen or lower alkyl, $R^7$ and $R^8$ each independently represent hydrogen or lower alkyl or $R^7$ and $R^8$ together represent lower alkylene in which one $CH_2$ group is optionally replaced by a hetero atom, X and Z each represent a spacer group, and n stands for 0, 1 or 2, and their pharmaceutically acceptable salts thereof, inhibit the release of tumor necrosis factor alpha (TNF-α) from cells. They can be used as medicaments, especially in the treatment of inflammatory and autoimmune diseases, osteoarthritis, respiratory diseases, tumors, cachexia, cardiovascular diseases, fever, haemorrhage and sepsis.

29 Claims, No Drawings

HYDRAZINE DERIVATIVES

BACKGROUND OF THE INVENTION

Release of such cytokines as tumor necrosis factor α (TNF-α) and transforming growth factor a (TNF-α) can cause adverse reactions ranging from psoriasis to sepsis. Many of these reactions are related to inflammanation or autoimmune conditions, such as psoriasis and arthritis.

Hydroxamic acid derivatives are known to have some inhibitory effect against certain cytokines, however they also inhibit matrix metalloproteinase enzymes (MPPs) such as collagenases, stromolysins, and gelatinases, leading to undesirable side effects. Thus it is desirable to find compounds capable of inhibiting TNF-α and TGF-α which do not have these side effects. In contrast to structurally related hydroxamic acid derivatives, the hydrazine derivatives provided by the present invention show only weak inhibitory activity against the matrix metalloproteinase (MMP) family of enzymes, such as collagenases, stromelysins and gelatinases.

SUMMARY OF THE INVENTION

The novel hydrazine derivatives provided by the present invention are compounds of the formula

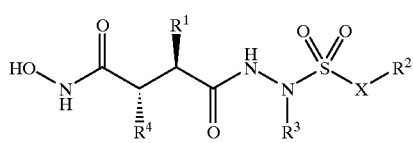

(I)

wherein
$R^1$ represents lower alkyl, lower alkenyl, lower cycloalkyl, lower cycloalkyl-lower alkyl, aryl or aryl-lower alkyl;
$R^2$ represents heterocyclyl or $NR^5R^6$;
$R^3$ represents hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
$R^4$ represents lower alkyl, lower alkenyl, lower cycloalkyl, lower cycloalkyl-lower alkyl or a grouping of the formula —Z-aryl, —Z-heterocyclyl or —$(CH_2)_n$—CH=$CR^7R^8$;
$R^5$ and $R^6$ each independently represent hydrogen or lower alkyl;
$R^7$ and $R^8$ each independently represent hydrogen or lower alkyl or $R^7$ and $R^8$ together represent lower alkylene in which one $CH_2$ group is optionally replaced by a hetero atom;
X and Z each represent a spacer group; and
n stands for 0, 1 or 2;
as well as mixtures of said compounds with one or more of their corresponding optical isomers and pharmaceutically acceptable salts of said compounds or said mixtures.

The hydrazine derivatives provided by the present invention are inhibitors of tumour necrosis factor alpha (TNF-α) release from cells. TNF-α has been associated with various cellular processes including inflammatory and cytotoxic processes. In particular TNF-α has been associated with inflammatory and autoimmune diseases (such as rheumatoid arthritis[1], inflammatory bowel disease[2], psoriasis[16,17]), osteoarthritis[5,6,] respiratory diseases (such as chronic obstructive pulmonary disease[7,8] and asthma[8,9]), tumor growth and angiogenesis[10], cachexia[11,12,] cardiovascular diseases (such as congestive heart failure[13,14]), dermatological diseases (such as graft-versus-host-disease[15] and), fever[18,19], haemorrhaue[20, 21] and sepsis[22]. Therefore the compounds of formula I are useful in treating the TNF-(X dependent cellular processes associated with these diseases.

The present invention is further directed the medicaments comprising a compound as described above or a pharmaceutically acceptable salt thereof and a therapeutically inert carrier material and to methods for making such medicaments.

The present invention is also directed the novel intermediates useful in the synthesis of the above described compounds.

Furthermore, the present invention is directed to a process for preparing compounds of formula (I).

In another aspect the present invention is directed to the use of a compound of formula (I) or a pharmaceutically acceptable salt thereof in the treatment of illnesses. In yet another aspect the present invention is directed to the use of a compound of formula (I) or a pharmaceutically acceptable salt thereof in the preparation or a medicament for the treatment of inflammatory and autoimmune diseases, osteoarthritis, respiratory diseases, tumors, cachexia, cardiovascular diseases, fever, haemorrhage and sepsis.

DETAILED DESCRIPTION OF THE INVENTION

As used herein, the term "lower alkyl", alone or in combination as in, for example, "halo-lower alkyl" or "lower cycloalkyl-lower alkyl", means a straight-chain or branched-chain alkyl group containing up to 8, preferably up to 4, carbon atoms, e.g. methyl, ethyl, n-propyl, isopropyl, n-butyl, isobutyl, sec.butyl, tert-butyl, n-pentyl and n-hexyl.

The term "halo-lower alkyl" means a lower alkyl group as defined earlier which carries one or more halogen atoms. Examples of halo-lower alkyl groups are chloro-methyl, trifluoromethyl and 2,2,2-trifluoroethyl.

The term "lower alkoxy", alone or in combination as in "lower alkoxycarbonyl", means a lower alkyl group as defined above which is bonded via an oxygen atom, e.g. methoxy, ethoxy, n-propoxy, isopropoxy, n-butoxy, isobutoxy and tert-butoxy.

Methoxycarbonyl, ethoxycarbonyl and the like are examples of lower alkoxycarbonyl groups.

The term "lower cycloalkyl", alone or in combination as in "lower cycloalkyl-lower alkyl", means a cycloalkyl group containing 3 to 7 carbon atoms, i.e. cyclopropyl, cyclobutyl, cyclopentyl, cyclohexyl and cycloheptyl. Cyclopropylmethyl, 2-cyclobutyl-ethyl and 3-cyclohexyl-propyl are examples of lower cycloalkyl-lower alkyl groups.

The term "lower alkenyl" means an alkenyl group containing from 2 to 7 carbon atoms, e.g. allyl, vinyl and butenyl.

The term "lower alkynyl" means an alkynyl group containing from 2 to 7 carbon atoms, e.g. propargyl or butynyl.

The term "aryl", alone or in combination as in "aryl-lower alkyl", means phenyl or naphthyl optionally substituted by halogen, i.e. fluorine, chlorine, bromine or iodine, lower alkyl, lower alkoxy, trifluoromethyl, hydroxy, lower alkoxycarbonyl, nitro, phenyl or the like, e.g. phenyl, 1-naphthyl, 2-methylphenyl, 4-methoxyphenyl, 2,4-difluorophenyl, 4-nitrophenyl and 4-methoxycarbonylphenyl. Benzyl, 4-chlorobenzyl, 4-bromobenzyl, 3-hydroxybenzyl, 4-methoxybenzyl, 4-nitrobenzyl, 2-phenylethyl, 3,4-dimethoxy-phenethyl and the like are typical examples of aryl-lower alkyl groups.

The term "heterocyclyl", alone or in combination as in "heterocyclyl-lower alkyl", means a 4-, 5-, 6- or 7-membered saturated or partially unsaturated or 5- or 6-membered aromatic heterocyclic ring which is bonded via a C atom or secondary N atom (i.e. —NH—), which contains one or more hetero atoms selected from nitrogen, sulphur and oxygen and/or a SO or $SO_2$ group and which is optionally substituted by up to four substituents, e.g. halogen, lower alkyl, lower alkoxy and/or oxo and/or optionally benz-fused. Preferably the heterocyclyl group contains from 1 to 4 heteroatoms. Examples of such heterocyclyl groups are pyrrolidinyl, pyrrolinyl, pyrazolinyl, piperidinyl, N-methylpiperidinyl, morpholinyl, thiamorpholinyl, thiamorpholinyl S,S-dioxide, hexahydroazepinyl, tetrahydropyranyl, tetrahydrothiopyranyl, furyl, thienyl, thiazolyl, oxazolyl, isoxazolyl, oxetanyl, imidazolidinyl, dioxolanyl, pyrrolyl, pyridyl, pyrimidinyl, benzofuranyl, benzothienyl, benzthiazolyl, indolyl, isoindolyl, e.g. phthalimido, quinolyl and isoquinolyl.

The term "heterocyclylcarbonyl" means a heterocyclyl group as previously defined which is bonded to C(O) via a secondary N atom. Morpholinocarbonyl is a typical example of such a heterocyclylcarbonyl group.

The term "heteroaryl" means an aromatic heterocyclic group within the definition of "heterocyclyl".

The term "halo" means fluoro, chloro, bromo or iodo unless specifically indicated to the contrary.

The spacer group denoted by X can be, for example, a group of the formula —$(CH_2)_{1-5}$— or —$(CH_2)_l$—Y—$(CH_2)_m$— in which l and m each independently stand for 0, 1 or 2 and Y represents arylene, lower cycloalkylene or heterocyclylene.

The spacer group denoted by Z can be, for example, a group of the formula —$(CH_2)_p$—W—$(CH_2)_q$— in which p and q each independently stand for 0, 1, 2 or 3 and W is absent or, preferably, represents —CH=CH—, —C≡C—, —S—, —O—, —NH—, —NHCO—, —CONH—, —$SO_2$—, —$NHSO_2$—, —$SO_2NH$—, —NHCONH— or —$NHSO_2NH$—.

The terms "arylene", "lower cycloalkylene", "lower alkylene" and "heterocyclylene" mean a divalent aryl, lower cycloalkyl, lower alkyl and, respectively, heterocyclyl group as herein before defined.

Compounds of formula I which are acidic form pharmaceutically acceptable salts with bases such as alkali metal hydroxides, e.g. sodium hydroxide and potassium hydroxide, alkaline earth metal hydroxides, e.g. calcium hydroxide, barium hydroxide and magnesium hydroxide, and the like. Those compounds of formula I which are basic can form pharmaceutically acceptable salts with inorganic acids, e.g. with hydrohalic acids such as hydrochloric acid and hydrobromic acid, sulphuric acid, nitric acid and phosphoric acid, and with organic acids, e.g. with acetic acid, tartaric acid, succinic acid, fumaric acid, maleic acid, malic acid, salicylic acid, citric acid methanesulphonic acid and p-toluenesulphonic acid.

It will be appreciated that, although the formulae presented herein show the respective compounds in their absolute stereochemistry, the invention embraces not only the depicted stereoisomers, but also the corresponding racemates and diastereoisomeric mixtures. The stereochemistry of the hydrazine derivatives of the present invention depends on the stereochemistry of the starting material of formula V from which it is made. Such starting materials can be made as in Example I (iii); or in Beckett et al, Synlett 1993,137; Larcheveque and Petit, Synthesis, 1991, 162; Bashiardes, et al., J. Organomet. Chem., 1989, 364, C29; Bashiardes et al., J. Chem. Soc. Perkin 1, 1989, 1162; or Fadel, et al., Tetrahedron Letts. 1988, 29, 6257–6260. The 1(S) compound is the preferred product or, in other terms, which are independent from the R or S terminology, it means that it is preferred that $R^4$ in a compound of formula (I) is "down" of the paper plane. Further, when the spacer group denoted by Z contains an olefinic double bond, as in —$CH_2$—CH=CH—, this can have the (E) or (Z) configuration, preferably the (E) configuration.

Preferred compounds of formula I are those in which $R^1$ represents lower alkyl, especially isobutyl. $R^2$ preferably represents pyridyl, especially 2-pyridyl, or $NR^5R^6$ in which $R^5$ and $R^6$ each represent a hydrogen atom or each represent a methyl group or an ethyl group or $R^5$ and $R^6$ together represent lower alkylene in which one $CH_2$ group is replaced by an oxygen atom, especially 3-oxapentamethylene (i.e. $R^2$ is morpholinyl). $R^3$ preferably represents lower alkyl, especially isobutyl. $R^4$ preferably represents a group of the formula -Z-aryl, especially in which Z represents —$(CH_2)_2$— or —$CH_2CH=CH$— and aryl represents phenyl. X preferably represents —$(CH_2)_{1-4}$— or —$CH_2$—Y in which Y represents arylene, especially phenylene and particularly o-phenylene.

Examples of preferred compounds provided by the present invention are:

(E)-2'-(2-Aminoethanesulphonyl)-2(R)-[1(S)-(hydroxycarbamoyl)-4-phenyl-3-butenyl]-2'-isobutyl-4-methylvalerohydrazide;

2'-(2-aminobenzenesulphonyl)-2(R)-[1(S)-(hydroxycarbamoyl)-4-phenylbutyl]-2'-isobutyl-4-methylvalerohydrazide;

(E)-2'-[3-(diethylamino)propylsulphonyl]-2(R)-[1(S)-(hydroxycarbamoyl)-4-phenyl-3-butenyl]-2'-isobutyl-4-methylvalerohydrazide;

(E)-2'-(3-aminopropanesulphonyl))-2(R)-[1(S)-(hydroxycarbamoyl)-4-phenyl-3-butenyl]-2'-isobutyl-4-methylvalerohydrazide;

(E)-2(R) -[1(S)-(hydroxycarbamoyl)-4-phenyl-3-butenyl]-2'-isobutyl-4-methyl-2'-[2-(2-pyridyl)ethanesulphonyl]valerohydrazide;

(E)-2(R)-[1(S)-(hydroxycarbamoyl)-4-phenyl-3-butenyl]-2'-isobutyl-4-methyl-2'-(3-morpholinopropylsulphonyl)valerohydrazide;

(E)-2(R)-[1(S)-(hydroxycarbamoyl)-4-phenyl-3-butenyl]-2'-isobutyl-4-methyl-2'-[3-(dimethylamino)propylsulphonyl]valerohydrazide; and (E)-2'-(4-aminobutanesulphonyl)-2(R)-[1(S)-(hydroxycarbamoyl)-4-phenyl-3-butenyl]-2'-isobutyl-4-methylvalerohydrazide.

According to the process provided by the invention, the novel hydrazine derivatives defined hereinbefore are manufactured by a) cleaving off the protecting group denoted by $R^9$ from a compound of the formula

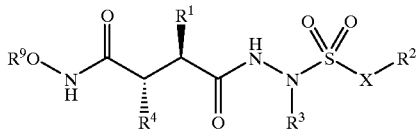

(II)

wherein $R^1$, $R^2$, $R^3$, $R^4$ and X have the significance given earlier and $R^9$ represents a protecting group, or b) for the manufacture of a compound of formula I in which $R^4$ represents —$CH_2CH_2CH_2$-aryl, X represents —$CH_2$-arylene and $R^2$ represents amino, cleaving off the protecting group denoted by $R^9$ from a compound of the formula

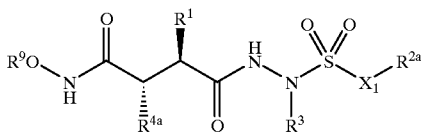

(III)

wherein $R^1$ and $R^3$ have the significance given earlier, $R^{4a}$ represents —$CH_2CH=CH$-aryl, $X_1$ represents —$CH_2$-arylene, $R^{2a}$ represents nitro and $R^9$ represents a protecting group, and reducing the resulting compound of the formula

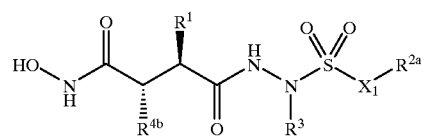

(IV)

wherein $R^1$, $R^{2a}$, $R^3$ and $X_1$ have the significance given earlier and $R^{4b}$ represents —$CH_2CH_2CH_2$-aryl, and c) if desired, converting a compound of formula I obtained into a pharmaceutically acceptable salt.

The protecting group denoted by $R^9$ in a compound of formula II can be any conventional protecting group, but is preferably tetrahydropyranyl, 4-methoxybenzyl, benzyl, or tri(lower alkyl)silyl, especially tert-butyldimethylsilyl.

The cleavage of the protecting group denoted by $R^9$ in a compound of formula II in accordance with embodiment a) of the process is carried out according to methods known per se. For example, the tetrahydropyranyl group can be cleaved off by treatment with a sulphonic acid, e.g.methanesulphonic acid or p-toluenesulphonic acid, in a lower alkanol, e.g. methanol, or by treatment with hydrogen chloride. Cleavage of the 4-methoxybenzyl group can be effected, for example, using trifluoroacetic acid. Hydrogenolysis in the presence of a catalyst, e.g. palladium, and in a lower alkanol, e.g. methanol, can be used for the cleavage of the benzyl group. A tri(lower alkyl)silyl group can be cleaved off using water or a medium having a low pH, with this cleavage normally taking place during the working up of the respective compound of formula II from the medium in which it is prepared (i.e. the cleavage takes place in situ).

The cleavage of the protecting group denoted by $R^9$ in a compound of formula III in accordance with the first step of embodiment b) of the process is carried out in a manner analogous to the cleavage of the protecting group denoted by $R^9$ in a compound of formula II described hereinbefore.

The reduction of a compound of formula IV in accordance with the second step of embodiment b) of the process is carried out in a manner known per se. For example, the reduction can be conveniently carried out using hydrogen in the presence of a conventional hydrogenation catalyst, e.g. a palladium catalyst such as palladium-on-carbon, and in an organic solvent which is inert under the hydrogenation conditions, e.g. a lower alkanol such as methanol, ethanol, etc. Preferably, the reduction is carried out at about room temperature and under atmospheric pressure. It is convenient to carry out the reduction without isolating the compound of formula IV from the medium in which it is prepared.

The conversion of a compound of formula I into a pharmaceutically acceptable salt in accordance with embodiment c) of the process is carried out in a known manner by treatment with an appropriate acid or base.

The compounds of formula II used as starting materials in embodiment a) of the foregoing process are novel and form a further object of the present invention. They can be prepared, for example, as illustrated in Reaction Scheme A in which $R^1$, $R^3$, $R^4$ and $R^9$ have the significances given earlier, $R^{20}$ has any of the values accorded to $R^2$ hereinbefore, provided that when $R^2$ contains a functional group that is reactive with the $SO_2CL$ group, e.g. a primary or secondary amino group (denoted by $NR^5R^6$)or hydroxy, $R^{20}$ is a protected form of such reactive functional group. Any conventional functional groups can be used, however, phthalimido is preferred. If there are no groups present that are reactive with the $SO_2Cl$ group, e.g. tertiary amine or a heterocycle with no free amino or hydroxy groups present, then protection is not required. P represents a protecting group, tBu represents tert-butyl and TFA represents trifluoroacetic acid.

Reaction Scheme A

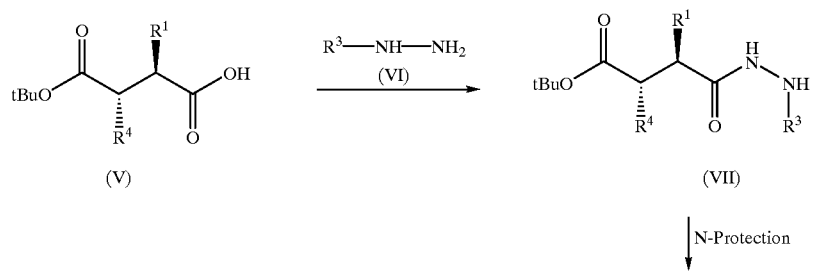

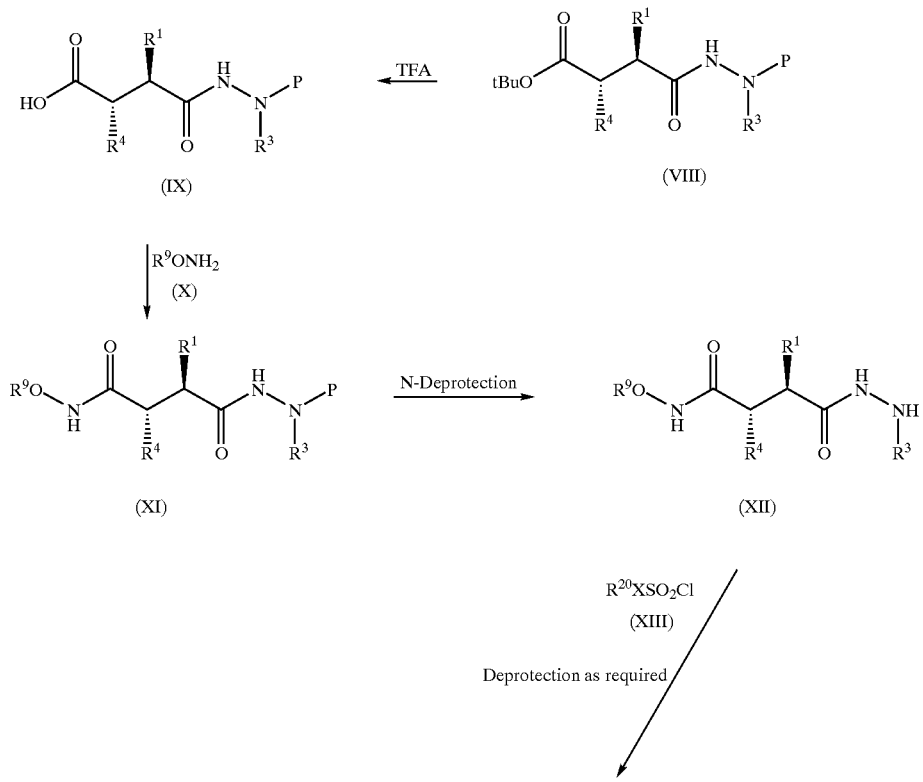

Having regard to Reaction Scheme A, the first step comprises the condensation of a compound of formula V with a compound of formula VI or an acid addition salt thereof, to give a hydrazide of formula VII. This condensation is carried out under the known conditions of a peptide coupling reaction and using the coupling reagents known per se for such couplings, e.g. 1-hydroxybenzotriazole in the presence of 1-ethyl-3-(3-dimethylaminopropyl) carbodiimide hydrochloride.

A hydrazide of formula VII is then N-protected in a known manner to give a compound of formula VIII. This protection can be by means of any conventional amino protecting group. It is, however, convenient to use trifluoroacetyl as the protecting group and to introduce this group by reacting a hydrazide of formula VII with trifluoroacetic anhydride, conveniently in an organic solvent which is inert under the reaction conditions, e.g. a halogenated hydrocarbon such as dichloromethane, and in the presence of an organic base, e.g. pyridine, at about room temperature.

In the next step a compound of formula VIII is deprotected with trifluoroacetic acid to give a carboxylic acid of formula IX. This deprotection is carried out in a manner known per se, e.g. in an organic solvent which is inert under the conditions of the reaction, such as a halogenated hydrocarbon, e.g. dichloromethane, at about room temperature.

Subsequently, a carboxylic acid of formula IX is converted into a compound of formula XI by condensation with an O-protected hydroxylamine of formula X. The condensation is carried out in a manner known per se for peptide coupling reactions and using conventional coupling reagents, e.g. 1-hydroxybenzotriazole in the presence of 1-ethyl-3-(3-dimethylaminopropyl)carbodiimide hydrochloride.

A compound of formula XI is then N-deprotected to give a compound of formula XII. The deprotection can be carried out in a manner known per se depending on the nature of the N-protecting group present. For example, when the N-protecting group is trifluoroacetyl, deprotection can be carried out using an aqueous alkali metal carbonate solution such as aqueous potassium carbonate solution.

Finally, a compound of formula XII is converted into a compound of formula II by reaction with a compound of formula XIII followed, where $R^{20}$ contains a protecting group, by deprotection at $R^{20}$. The reaction of a compound of formula XII with a compound of formula XIII is carried out in a conventional manner, conveniently in an organic solvent which is inert under the reaction conditions and in the presence of an organic base at about 0° C. to about room temperature. Suitable solvents include halogenated hydrocarbons, e.g. dichloromethane. Pyridine can be mentioned as an example of a suitable organic base which can be used. Any deprotection at $R^{20}$ which is required after the reaction can be carried out in a known manner depending on the nature of the protecting group present. For example, phthalimido can be converted into amino by treatment with hydrazine hydrate.

In an alternative procedure for the preparation of compounds of formula II in which X represents $-(CH_2)_{1-5}-$ and $R^2$ represents $NR^5R^6$ in which $R^5$ and $R^6$ both represent lower alkyl, a compound of formula XII is firstly reacted with a compound of the formula $Cl-(CH_2)_{1-5}-SO_2Cl$, conveniently in an organic solvent which is inert under the reaction conditions, e.g. a halogenated hydrocarbon such as dichloromethane, and in the presence of an organic amine, e.g. pyridine. The reaction product obtained, a compound corresponding to formula II in which X represents $-(CH_2)_{1-5}-$ and $R^2$ represents chlorine, is then reacted with a di(lower alkyl)amine, e.g. diethylamine, in the presence of sodium iodide and in a solvent which is inert under the reaction conditions, e.g. a ketone such as methyl ethyl ketone, at an elevated temperature, e.g. at reflux, to give the desired starting material of formula II in which X represents —$(CH_2)_{1-5}$— and $R^2$ represents $NR^5R^6$ in which $R^5$ and $R^6$ both represent lower alkyl.

If desired, compounds occurring in or prepared by Reaction Scheme A can be interconverted or substituted.

For example, a compound of formula V in which $R^4$ represents a group of the formula —$CH_2$—CH=CH-aryl can be converted into a corresponding compound of formula III in which $R^4$ represents a different group of the formula —$CH_2$—CH=CH-aryl or —$CH_2$—CH=CH-heteroaryl by reaction with ozone at a low temperature, e.g. −78° C., in an organic solvent which is inert under the conditions of the reaction, e.g. a halogenated hydrocarbon such as dichloromethane and subsequent reaction with dimethyl sulphide and an appropriate Wittig reagent.

Again, for example, a compound of formula VII in which $R^3$ represents hydrogen can be converted into a corresponding compound of formula VII in which $R^3$ represents lower alkyl, lower alkenyl, lower alkynyl, lower cycloalkyl or aryl-lower alkyl in a manner known per se. For example, a compound of formula VII in which $R^3$ represents hydrogen can be condensed with an aldehyde of the formula $R^{30}$—CHO, wherein $R^{30}$ represents lower alkyl, lower alkenyl, lower alkynyl, lower cycloalkyl or aryl-lower alkyl, e.g. in the presence of p-toluenesulphonic acid and molecular sieves, and the resulting substituted imine can be reduced, preferably in situ, using an alkali metal cyanoborohydride, especially sodium cyanoborohydride.

Moreover, a compound of II in which $R^3$ represents hydrogen can be converted into a corresponding compound of formula II in which $R^3$ represents lower alkyl, lower alkenyl, lower alkynyl, lower cycloalkyl or aryl-lower alkyl by reaction with a halide of the formula $R^{30}$—X, wherein $R^{30}$ has the significance given earlier and X represents halogen, conveniently in the presence of a base, e.g. an alkali metal carbonate such as sodium carbonate or potassium carbonate, and in an organic solvent which is inert under the conditions of the reaction, e.g. dimethylformamide.

The compounds of formula III used as starting materials in embodiment b) of the foregoing process and the compounds of formula IV, which occur as intermediates, are novel and form further objects of the present invention. The compounds of formula III can be prepared, for example, by reacting a compound of formula XII hereinbefore with a nitro compound of the formula $O_2N$—$X_1$—$SO_2Cl$, wherein Xl has the significance given earlier. The reaction is carried out in an analogous manner to that described earlier in connection with the reaction of a compound of formula XII with a compound of formula XIII.

The compounds of formulae V, VI, X and XIII hereinbefore as well as the aldehydes of the formula $R^{30}$—CHO, the halides of formula $R^{30}$-X and the nitro lo compound of the formula $O_2N$—$X_1$—$SO_2Cl$ are known compounds or analogues of known compounds which can be prepared in an analogous manner analogous to the known compounds.

In particular, the compounds of formula V can be prepared by methods disclosed in published patent applications EP-497192-A and EP-574758-A and also using the methods of Beckett et al, Synlett 1993, 137 and Pratt et al, Synlett 1998, 531.

The compounds of formula VI can be obtained from commercial suppliers (e.g. methyl hydrazine, Aldrich cat. no. M5,000-1; benzyl hydrazine diHCl, Aldrich cat. no. B2,285-2; phenelzine HCl, Sigma cat. no. P6,777; N-propyl hydrazine HCl, Ubichem cat. no. 002665), or be prepared by the method of Zwierzak, Synthesis 1987, 485.

The compounds of formula X can be obtained from commercial suppliers (e.g. O-benzylhydroxylamine HCl, Aldrich cat. no. B2,298-4; O-(tetrahydro-2H-pyran-2-yl) hydroxylamine, Aldrich cat. no. 48,089-4; O-(trimethylsilyl) hydroxylamine, Aldrich cat. no. 44,044-2), or be prepared by the method of Teodozyl et al, Rocz. Chem. 1976, 50(2), 367 (CAN 85:62908).

The compounds of formula XIII can be obtained from commercial suppliers (e.g. 2-phthalimidoethanesulfonyl chloride, Asta Tech, Inc. cat. no. N88865), or be prepared from commercially available sulfonic acids (e.g. 2-(2-pyridyl)ethanesulfonic acid, Aldrich cat. no. 30,392-5; N-(morpholinyl)ethanesulfonic acid, Sigma cat. no. M3023) by methods well known in the art such as treatment with PCl5, or by adaptation of the methods provided by Atwell G. J., Cain B. F. and Denny W. A., J.Med.Chem. 1977,20, 128–134; and Kricheldorf H. R. and Schultz J., Synthesis 1976,11, 739–741.

The compounds of formula $R^{30}$—CHO can be obtained from commercial suppliers (e.g. benzaldehyde, Aldrich cat. no. B133-4; isobutryaldehyde, Aldrich cat. no. 32,035-8), or be prepared by methods well known in the art, see Organic Chemistry $3^{rd}$ Edition by Fieser and Fieser, Reinhold Publishing, New York, preparation of aldehydes p193–198 and 675–684; Compendium of Organic Synthetic Methods Volume 1 by Harrison and Harrison, Wiley-Interscience, Chapter 4, Preparation of Aldehydes.

The compounds of formula $R^{30}$—X can be obtained from commercial suppliers (e.g. benzyl bromide, Aldrich cat. no. B1,790-5; 1-bromo-2-methylpropane, Aldrich 15,658-2), or be prepared by methods well known in the art, see Organic Chemistry $3^{rd}$ Edition by Fieser and Fieser, Reinhold Publishing, New York, preparation of alkyl halides p61–63 and 145–146; Compendium of Organic Synthetic Methods Volume 1 by Harrison and Harrison, Wiley-Interscience, Chapter 10, Preparation of Halides and Sulfonates.

The compounds of formula $O_2N$—$X_1$—$SO_2Cl$ can be obtained from commercial suppliers (e.g. 2-nitro-alpha-toluenesufonyl chloride, Aldrich cat. no.37,582-9), or be prepared from commercially available benzyl halides by the methods described in U.S. Pat. No. 3,471,474 and EP 0 514 66 A2.

As mentioned earlier, the hydrazine derivatives provided by the present invention inhibit the release of TNF-α from mammalian cells. This can be demonstrated using the in vitro test procedure described hereinafter:

THP1 cells were cultivated in RPMI 1640 medium supplemented with antibiotics and 10% foetal calf serum, harvested by centrifugation and diluted to $5 \times 10^5$ cells/ml in the above medium supplemented with 20 mM HEPES buffer. Aliquots (200 microliters) of the cell suspension were plated out on 96 well culture plates and incubated for 0.5 hour at 37° C. prior to the addition of the test compounds. The latter were dissolved in dimethyl sulphoxide (DMSO) to a stock concentration of 1.2 mM which was diluted with phosphate buffered saline/10% DMSO solution to provide test compounds in final concentrations of $10^{-9}$ to $10^{-5}$ M, with each concentration being tested in duplicate. The cells were incubated with the test compounds for 0.5 hour at 37° C., LPS (bacterial lipopolysaccharide) was then added to a concentration of 2 mg/ml and incubation was continued for 3 hours at 37° C. in an atmosphere containing 5% $CO_2$ and at 95% relative humidity. After centrifugation at 260 g for 10 minutes an aliquot of each supernatant was removed and the amount of TNF-α was estimated by ELISA (R & D Systems Europe Ltd., Abingdon, England). The concentration of test compound which brings about 50% inhibition of LPSinduced TNF-α release (IC50) was computed from the dose-response curve.

Compounds A–E listed hereinafter have an $IC_{50}$ of 318–866 nMol in the foregoing test procedure:

Compound A:
2'-(2-aminobenzenesulphonyl)-2(R)-[1(S)-(hydroxycarbamoyl)-4-phenylbutyl]-2'-isobutyl-4-methylvalerohydrazide p-toluenesulphonate.

Compound B:
(E)-2'-[3-(Diethylamino)propylsulphonyl]-2(R)-[1(S)-(hydroxycarbamoyl)-4-phenyl-3-butenyl]-2'-isobutyl-4-methylvalerohydrazide p-toluenesulphonate.

Compound C:
(E)-2'-(3-Aminopropanesulphonyl)-2(R)-[1(S)-(hydroxycarbamoyl)-4-phenyl-3-butenyl]-2'-isobutyl-4-methylvalerohydrazide p-toluenesulphonate.

Compound D:
(E)-2(R)-[1(S)-(Hydroxycarbamoyl)-4-phenyl-3-butenyl]-2'-isobutyl-4-methyl-2'-[3-(dimethylamino)propylsulphonyl]valerohydrazide p-toluenesulphonate.

Compound E:
(E)-2'-(4-Aminobutanesulphonyl)-2(R)-[1(S)-(hydroxycarbamoyl)-4-phenyl-3-butenyl]-2'-isobutyl-4-methylvalerohydrazide p-toluenesulphonate.

The hydrazine derivatives provided by the present invention (i.e. the compounds of formula I and their pharmaceutically acceptable salts), can be used as medicaments, for example in the form of pharmaceutical preparations. The pharmaceutical preparations can be administered orally, e.g. in the form of tablets, coated tablets, dragees, hard and soft gelatine capsules, solutions, emulsions or suspensions. However, they can also be administered rectally, e.g. in the form of suppositories, or parenterally, e.g. in the form of injection solutions.

For the manufacture of pharmaceutical preparations the hydrazine derivatives can be formulated with therapeutically inert, inorganic or organic carriers. Lactose, corn starch or derivatives thereof, talc, stearic acid or its salts can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories.

The pharmaceutical preparations can also contain preservatives, stabilizers, wetting agents, emulsifiers, sweeteners, colorants, flavorants, salts for adjustment of the osmotic pressure, buffers, masking agents or antioxidants. They may also contain other therapeutically active substances.

Medicaments containing an aforementioned hydrazine derivative and a therapeutically acceptable carrier as well as a process for the manufacture of such medicaments are also objects of the present invention. This process comprises bringing a compound of formula I or a pharmaceutically acceptable salt thereof into a galenical administration form together with a therapeutically inert carrier material and, if desired, one or more additional therapeutically active substances.

The compounds of formula (I) and the pharmaceutically acceptable salts thereof are all inhibitors of TNF-α release. Therefore, the compounds of the invention are anti-inflammatory agents which can be used in combating the inflammatory condition which occur in various diseases caused by an excess of TNF-α.

Therefore, a further object of the invention comprises the use of the hydrazine derivatives provided by the invention in the treatment of inflammatory and autoimmune diseases (e.g. rheumatoid arthritis, inflammatory bowel disease, multiple sclerosis and psoriasis), osteoarthritis, respiratory diseases (e.g. asthma and chronic obstructive pulmonary disease), tumors, cachexia, cardiovascular diseases (e.g. congestive heart failure), fever, haemorrhage and sepsis. The dosage can vary within wide limits and will, of course, be adjusted to the individual requirements in each particular case. In general, in the case of administration to adults, a daily dosage of about 1–20 mg/kg, preferably about 3–5 mg/kg, should be appropriate, although the upper limit may be exceeded when this is found to be expedient. The daily dosage can be administered as a single dosage or in divided dosages.

The contents of Great Britain Patent Application No. 9826153.0, filed Nov. 27, 1998 are incorporated herein by reference.

The following Examples illustrate the present invention, without limiting it.

EXAMPLE 1

2'-(2-Aminobenzylsulphonyl)-2(R)-[1(S)-(hydroxycarbamoyl)-4-phenylbutyl]-2'-isobutyl-4-methylvalerohydrazide p-toluenesulphonate A solution of 0.35 g of (E)-2(R)-[1(S)-[(tetrahydro-2(RS)-pyranyloxy)-carbamoyl]-4-phenyl-3-butenyl]-2'-isobutyl-4-methyl-2'-(2-nitrobenzylsulphonyl)valerohydrazide in 10 ml of methanol was treated with 0.101 g of p-toluenesulphonic acid monohydrate. The mixture was stirred at room temperature for 1.5 hours and then 0.035 g of 10% palladium-on-carbon was added. The mixture was hydrogenated for 1 hour, then filtered and the filtrate was evaporated. Trituration of the residue with diethyl ether gave 0.27 g of 2'-(2-aminobenzylsulphonyl)-2(R)-f [(S)-(hydroxycarbamoyl)-4-phenylbutyl]-2'-isobutyl-4-methyl-valerohydrazide p-toluenesulphonate in the form of a white solid.

MS: 547 $(M+H)^+$.

HPLC: Gradient elution using solvent A containing 5% solvent B increasing to 95% solvent B over 15 minutes; flow rate 1 ml per minute. Retention time: 13.15 minutes. Solvent A: $H_2O/0.1\%$ TFA; solvent B: $CH_3CN/0.085\%$ TFA. Column type: HYPERPEP 300A.

The (E)-2(R)-[1(S)-[(tetrahydro-2(RS)-pyranyloxy) carbamoyl]-4-phenyl-3-butenyl]-2'-isobutyl-4-methyl-2'-(2-nitrobenzylsulphonyl)valerohydrazide used as the starting material was prepared as follows:

(i) A solution of 253.3 g of 4-tert-butyl hydrogen 2(R)-isobutylsuccinate in 2 l of dry tetrahydrofuran was cooled to −70° C. while stirring under nitrogen. 1.2 l of a 2M solution of lithium diisopropylamide in tetrahydrofuran was added dropwise and the mixture was stirred at −70° C. for 30 minutes. A solution of 282 g of cinnamyl bromide in 2 l of dry tetrahydrofuran was then added dropwise and the mixture was left to come to room temperature gradually. After stirring overnight the tetrahydrofuran was evaporated and the residue was partitioned between ethyl acetate and 2M hydrochloric acid solution. The ethyl acetate layer was washed with a further portion of 2M hydrochloric acid solution, water and saturated sodium chloride solution and then dried over anhydrous magnesium sulphate. The solvent was evaporated to give a gummy solid. This was suspended in 2 l of hexane and the product was removed by filtration (crop 1:77.3 g). The hexane solution was treated with 109 g of cyclohexylamine and the mixture was left to stand for 1 hour at room temperature and for 16 hours at 4° C. The solid which formed was filtered off and dissolved in 2.5 l of methyl tert.butyl ether and 1.5 l of 2M hydrochloric to give a clear solution. The organic phase was washed twice with water and with saturated sodium chloride solution and then dried over anhydrous magnesium sulphate. After evaporation of the solvent there were obtained 189.8 g of a solid (crop 2).The two crops were combined and dried to give 267.1 g of (E)-2(R)-[(R)-(tert-butoxycarbonyl)-4-phenyl-3-butenyl]-4-methylvaleric acid in the form of a pale cream coloured solid.

(ii) The compound obtained in part (i) was dissolved in 2.5 l of dry tetrahydrofuran, cooled to −78° C. while stirring and 860 ml of a 2M solution of lithium diisopropylamide in tetrahydrofuran were added dropwise over 2 hours. After stirring for 0.5 hours at −78° C. 330 ml of methanol were added dropwise. The mixture was left to come to room temperature gradually and was then stirred overnight. The tetrahydrofuran was evaporated and the residue was partitioned between ethyl acetate and 2M hydrochloric acid solution. The ethyl acetate phase was washed in succession with two further portions of hydrochloric acid solution, two portions of water and saturated sodium chloride solution and dried over magnesium sulphate. After evaporation there was obtained an orange oil which contained a mixture of the 1(S),2(R) and 1(R),2(R) isomers of E-2-[1-(tert-butoxycarbonyl)-4-phenyl-3-butenyl]-4-methylvaleric acid. The above epimerization procedure was repeated three times to give a mixture substantially enriched in the 1 (S),2(R) isomer. The crude product was dissolved in 2500 ml of hexane and the solution was treated with 89 ml of tert.butylamine. After leaving to stand at 4° C. the precipitated salt was filtered off and dried. There were obtained 210.3 g of a pale cream solid which was converted into the free acid by the procedure described above to give (E)-2(R)-[1(S)-(tert-butoxycarbonyl)-4-phenyl-3-butenyl]-4-methylvaleric acid in the form of a yellow solid.

(iii) A solution of 4.05 kg of (E)-2(R)-[1(S)-(tert-butoxycarbonyl) -4-phenyl-3-butenyl]-4-methylvaleric acid in 12 l of dimethylformamide was cooled to 4° C. and treated with 1.97 kg of hydroxybenzotriazole hydrate and 2.466 kg of 1-ethyl-3-(3-dimethylaminopropyl)carbodiimide hydrochloride and the solution was stirred for 2 hours at 4° C. 3.895 kg of isobutylhydrazine di-tosylate salt were added followed by 2.36 l of N-methylmorpholine The mixture was stirred for 2 hours at 4° C. and for 50 hours at room temperature, diluted with 12 l of 2M hydrochloric acid and 12 l of methyl tert.butyl ether and the organic phase was separated. The organic phase was washed with water, saturated sodium hydrogen carbonate solution and water and then evaporated to give a dark cream solid. Recrystallization from hexane gave 2.47 kg of (E)-2(R)-[1 (S)-(tert-butoxycarbonyl)-4-phenyl-3-butenyl]-2'-isobutyl-4-methyl-valerohydrazide in the form of a cream solid.

MS: 417 (M+H)$^+$.

(iv) A solution of 40.0 g of (E)-2(R)-[1(S)-(tert-butoxycarbonyl)-4-phenyl-3-butenyl]-2'-isobutyl-4-methylvalerohydrazide and 11.2 ml of pyridine in 400 ml of dichlomethane was stirred under a nitrogen atmosphere. 16.3 ml of trifluoroacetic anhydride were added and the mixture was stirred for 10 minutes at room temperature and evaporated. The residue in ethyl acetate was washed with 5% sodium hydrogen carbonate solution, water, 2M aqueous hydrochloric acid and water. The ethyl acetate phase was dried over anhydrous magnesium sulphate and the solvent was evaporated to give 55 g of (E)-2(R)-[1(S)-(tert-butoxycarbonyl)-4-phenyl-3-butenyl]-2'-isobutyl-2'-(trifluoroacetyl)-4-methylvalerohydrazide as a dark orange gum.

MS: 513 (M+H)$^+$.

(v) The crude tert.butyl ester obtained according to (iv) was dissolved in 250 ml of a 40% solution of trifluoroacetic acid in dichloromethane and stirred at room temperature for 2.5 hours. The solvent was evaporated and traces of trifluoroacetic acid were removed by the addition and evaporation of toluene (2×30 ml). The residue was triturated with hexane to give 39.1 g of (E)-2(R)-[1(S)-(carboxy)-4-phenyl-3-butenyl]-2'-isobutyl-2'-(trifluoroacetyl)-4-methylvalerohydrazide in the form of an off-white solid.

(vi) The carboxylic acid prepared in the preceding paragraph was dissolved in 90 ml of dimethylformamide, cooled to 0° C. and treated in succession with 50.0 g of O-(tetrahydro-2H-pyran-2(RS)-yl)hydroxylamine and 18.0 g of 1-ethyl-3-(3-dimethylaminopropyl)carbodiimide hydrochloride. The mixture was left to come to room temperature and was stirred overnight. The solvent was evaporated and the residue was partitioned between ethyl acetate and water. The ethyl acetate phase was washed with water until neutral, dried over anhydrous magnesium sulphate and evaporated. The resulting solid was triturated with hexane and filtered off to give 37.6. g of (E)-2(R)-[1(S)-[(tetrahydro-2(RS)-pyranyloxy)carbamoyl]-4-phenyl-3-butenyl]-2'-isobutyl-2'-(trifluoroacetyl)-4-methylvalerohydrazide in the form of a white solid.

(vii) The compound obtained according to part (vi) was dissolved in 200 ml of methanol and treated with a solution of 18.7 g of potassium carbonate in 50 ml of water for 16 hours at room temperature. Removal of the methanol by evaporation gave a solid, which was washed with water and dried in vacuo over solid sodium hydroxide to yield 28.2 g of (E)-2(R)-[1(S)-[(tetrahydro-2(RS)-pyranyloxy)carbamoyl]-4-phenyl-3-butenyl]-2'-isobutyl-4-methylvalerohydrazide as a white solid.

MS: 460 (M+H)$^+$.

HPLC: Gradient elution using solvent A containing 5% solvent B increasing to 95% solvent B over 15 minutes; flow rate 1 ml/minute. Retention time: 12.46 minutes. Solvent A: H20/0. I% TFA; solvent B: CH3CN/0.085% TFA. Column type: HYPERPEP 300A.

(viii) A solution of 0.689 g of (E)-2(R)-[1(S)-[(tetrahydro-2(RS) -pyranyloxy)carbamoyl]-4-phenyl-3-butenyl]-2'-isobutyl-4-methylvalerohydrazide in 8 ml of dichloromethane was treated with 0.236 g of 2-nitro-α-toluenesulphonyl chloride and 0.152 ml of pyridine at room temperature and under a nitrogen atmosphere. The mixture was stirred for 2 hours and evaporated. The residue was dissolved in ethyl acetate and washed in sequence with water, 5% aqueous citric acid, water, 5% aqueous sodium hydrogen carbonate and saturated aqueous sodium chloride and then dried over anhydrous magnesium sulphate. Evaporation and trituration of the residue with diethyl ether gave 0.72 g of (E)-2(R)-[1(S)-[(tetrahydro-2(RS)-pyranyloxy)carbamoyl]-4-phenyl-3-butenyl]-2'-isobutyl-4-methyl-2'-(2-nitrobenzylsulphonyl)valerohydrazide in the form of a white solid.

MS: 659 (M+H)$^+$.

EXAMPLE 2

(E)-2'-(2-Aminoethanesulphonyl)-2(R)-[1(S)-(hydroxycarbamoyl)-4-phenyl-3-butenyl]-2'-isobutyl-4-methylvalerohydrazide p-toluenesulphonate A solution of 0.25 g of (E)-2'-(2-aminoethanesulphonyl)-2(R)-[1(S)-[(tetrahydro-2(RS)-pyranyloxy)carbamoyl]-4-phenyl-3-butenyl]-2'-isobutyl-4-methylvalerohydrazide in 5 ml of methanol was treated with 0.1 g of p-toluenesulphonic acid monohydrate. The mixture was stirred for 2.5 hours at room temperature and evaporated. The residue was triturated with diethyl ether, filtered off and dried to give 0.255 g of (E)-2'-(2-aminoethanesulphonyl)-2(R)-[1(S)-(hydroxycarbamoyl)-4-phenyl-3-butenyl]-2'-isobutyl-4-methylvalerohydrazide p-toluene-sulphonate in the form of a white solid.

MS: 483 $(M+H)^+$.

HPLC: Gradient elution using solvent A containing 5% solvent B increasing to 95% solvent B over 15 minutes; flow rate 1 ml/minute. Retention time: 11.22 minutes. Solvent A: $H_2O$/0.1% TFA; solvent B: $CH_3CN$/0.085% TFA. Column type: HYPBDSC18.

The (E)-2'-(2-aminoethanesulphonyl)-2(R)-[1(S)-[(tetrahydro-2(RS)-pyranyloxy)carbamoyl ]-4-phenyl-3-butenyl]-2'-isobutyl-4-methylvalerohydrazide used as the starting material was prepared as follows:

(i) A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 8 ml of dichloromethane was treated with 0.287 g of 2-phthalimidoethanesulphonyl chloride and 0.1 ml of pyridine at room temperature under a nitrogen atmosphere. The mixture was stirred for 2 hours at room temperature and a further 0.287 g of 1,3-dioxo-2-phthalimidoethanesulphonyl chloride was added. The mixture was stirred overnight at room temperature and evaporated. The residue was dissolved in ethyl acetate and washed in sequence with water, 5% aqueous citric acid, water, 5% aqueous sodium hydrogen carbonate and saturated aqueous sodium chloride. Drying over anhydrous magnesium sulphate and evaporation gave a residue which was triturated with diethyl ether to give 0.47 g of (E)-2(R)-[1(S)-[(tetrahydro-2(RS)-pyranyloxy)carbamoyl]-4-phenyl-3-butenyl]-2'-isobutyl-2'-(1,3-dioxo-2-phthalimidoethanesulphonyl)-4-methylvalerohydrazide in the form of a pale yellow solid.

MS: 697 $(M+H)^+$.

(ii) A solution of 0.46 g of (E)-2(R)-[1(S)-[(tetrahydro-2(RS)-pyranyloxy)carbamoyl]-4-phenyl-3-butenyl]-2'-isobutyl-2'-(1,3-dioxo-2-phthalimidoethansulphonyl)-4-methylvalerohydrazide in 10 ml of ethanol was treated with 4.5 ml of hydrazine hydrate and stirred at room temperature for 2 hours. Evaporation gave a residue which was triturated with ethyl acetate and filtered. The filtrate was washed with water and saturated aqueous sodium chloride and then dried over anhydrous magnesium sulphate. The residue was purified by column chromatography on silica gel using methanol/dichloromethane (5:95) for the elution to give 0.26 g of (E)-2'-(2-aminoethanesulphonyl)-2(R)-[1(S)-[(tetrahydro-2(RS)-pyranyloxy)carbamoyl]-4 -phenyl-3-butenyl]-2'-isobutyl-4-methylvalerohydrazide in the form of a pale yellow gum.

MS: 567 $(M+H)^+$.

EXAMPLE 3

(E)-2'-(3-Aminopropanesulphonyl)-2(R)-[1(S)-(hydroxycarbamoyl)-4-phenyl-3-butenyl]-2'-isobutyl-4-methylvalerohydrazide p-toluenesul phonate In a manner analogous to that described in Example 2, but using 3-phthalimidopropanesulphonyl chloride in the place of 2-phthalimidoethanesulphonyl chloride, there was obtained (E)-2'-(3-aminopropanesulphonyl)-2(R)-[1(S)-(hydroxycarbamoyl)-4-phenyl-3-butenyl]-2'-isobutyl-4-methylvalerohydrazide p-toluenesulphonate in the form of an off-white solid.

MS: 497 $(M+H)^+$.

HPLC: Gradient elution using solvent A containing 5% solvent B increasing to 95% solvent B over 15 minutes; flow rate 1 ml/minute. Retention time: 11.21 minutes. Solvent A: $H_2O$/0.1% TFA; solvent B: $CH_3CN$/0.085% TFA. Column type: HYPBDSC18.

EXAMPLE 4

(E)-2'-(4-Aminobutanesulphonyl)-2(R)-[1(S)-(hydroxycarbamoyl)-4-phenyl-3-butenyl]-2'-isobutyl-4-methylvalerohydrazide p-toluenesulphonate In a manner analogous to that described in Example 2 but using 4-phthalimidobutanesulphonyl chloride in the place of 2-phthalimidoethanesulphonyl chloride, there was obtained (E)-2'-(4-aminobutanesulphonyl)-2(R)-[1(S)-(hydroxycarbamoyl)-4-phenyl-3-butenyl]-2'-isobutyl-4-methylvalerohydrazide p-toluene-sulphonate in the form of a white solid.

MS: 511 $(M+H)^+$.

HPLC: Gradient elution using solvent A containing 5% solvent B increasing to 95% solvent B over 15 minutes; flow rate 1 ml/minute. Retention time: 11.31 minutes. Solvent A: $H_2O$/0.1% TFA; solvent B: $CH_3CN$/0.085% TFA. Column type: $HYPBDSC_{18}$.

EXAMPLE 5

(E)-2(R)-[1(S)-(Hydroxycarbamoyl)-4-phenyl-3-butenyl]-2'-isobutyl-4-methyl-2'-[2-(2-pyridyl)ethanesulphonyl] valerohydrazide hydrochloride A solution of 0.547 g of (E)-2(R)-[1(S)-[(tetrahydro-2(RS)-pyranyloxy)carbamoyl]-4-phenyl-3-butenyl]-2'-isobutyl-4-methyl-2'-[2-(2-pyridyl)ethanesulphonyl]-valerohydrazide in 5 ml of methanol was treated with 4 ml of a 1 M solution of hydrogen chloride in dioxan. The mixture was stirred at room temperature for 3 hours and evaporated. The residue was triturated with diethyl ether to give 0.463 g of (E)-2(R)-[1(S)-(hydroxycarbamoyl)-4-phenyl-3-butenyl]-2'-isobutyl-4-methyl-2'-[2-(2-pyridyl)ethanesulphonyl]valerohydrazide hydrochloride in the form of a white solid.

MS: 545 $(M+H)^+$.

HPLC: Gradient elution using solvent A containing 5% solvent B increasing to 95% solvent B over 15 minutes; flow rate 1 ml/minute. Retention time: 11.33 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-2'-isobutyl-4-methyl-2'-[2-(2-pyridyl)ethanesulphonyllvalerohydrazide used as the starting material was prepared as follows:

A solution of 0.459 g of (E)-2(R)-[1(S)-[(tetrahydro-2(RS)-pyranyloxy)carbamoyl]-4-phenyl-3-butenyl]-2'-isobutyl-4-methylvalerohydrazide in 10 ml of dichloromethane was treated with 0.400 ml of pyridine and 0.337 g of 2-(2-pyridine)ethanesulphonyl chloride. The mixture was stirred overnight at room temperature. A further 0.1 g of 2-(2-pyridine)ethanesulphonyl chloride and 0.4 ml of pyridine were added and the mixture was stirred for a further 3 days at room temperature. Evaporation gave a residue which was dissolved in ethyl acetate and washed with 5% aqueous sodium hydrogen carbonate and saturated aqueous sodium chloride. Drying over anhydrous magnesium sulphate, evaporation and trituration with ether/hexane gave 0.547 g of (E)-2(R)-[1(S)-[(tetrahydro-2(RS)-pyranyloxy) carbamoyl]-4-phenyl-3-butenyl]-2'-isobutyl-4-methyl-2'-[2-(2-pyridyl)ethanesulphonyl]valerohydrazide in the form of a white solid.

MS: 629 (M+H)+.

EXAMPLE 6

(E)-2(R)-[1(S)-(Hydroxycarbamoyl)-4-phenyl-3-butenyl]-2'-isobutyl-4-methyl-2'-(3-(4-morpholino) propylsulphonyl-)valerohydrazide hydrochloride In a manner analogous to that described in Example 5, but using 3-(4-morpholinepropanesulphonyl chloride in the place of 2-(2-pyridine)ethanesulphonyl chloride, there was obtained (E)-2(R)-[1(S)-(hydroxycarbamoyl)-4-phenyl-3-butenyl]-2'-isobutyl-4-methyl-2'-(3-(4-morpholino) propylsulphonyl)valerohydrazide hydrochloride in the form of a white solid.

MS: 567 (M+H)+.

HPLC: Gradient elution using solvent A containing 5% solvent B increasing to 95% solvent B over 15 minutes; flow rate 1 ml/minute. Retention time: 11.28 minutes. Solvent A: $H_2O$/0.1% TFA; solvent B: $CH_3CN$/0.085% TFA. Column type: HYPERPEP 300A.

EXAMPLE 7

(E)-2'-[3-(Dimethylamino)propylsulphonyl]-2(R)-[1(S)-(hydroxycarbamoyl)-4-phenyl-3-butenyl]-2'-isobutyl-4-methylvalerohydrazide p-toluenesulphonate A solution of 0.184 g of (E)-2'-[3-(dimethylamino) propylsulphonyl]-2(R)-[1(S)-[(tetrahydro-2(RS)-pyranyloxy)carbamoyl]-4-phenyl-3-butenyl]-2'-isobutyl-4-methylvalerohydrazide in 4 ml of methanol was treated with 0.069 g of p-toluene-sulphonic acid monohydrate. The mixture was stirred for 3.5 hours at room temperature and evaporated. Trituration of the residue with diethyl ether gave 0.19 g of (E)-2'-[3-(dimethylamino)propylsulphonyl]-2(R)-[1(S)-(hydroxycarbamoyl)-4-phenyl-3-butenyl]-2'-isobutyl-4-methylvalerohydrazide p-toluenesulphonate in the form of an off-white solid.

MS: 525 (M+H)+.

HPLC: Gradient elution using solvent A containing 5% solvent B increasing to 95% solvent B over 15 minutes; flow rate 1 ml/minute. Retention time: 11.33 minutes. Solvent A: $H_2O$/0.1% TFA; solvent B: $CH_3CN$/0.085% TFA. Column type: HYPERPEP 300A.

The (E)-2'-[3-(dimethylamino)propylsulphonyl]-2(R) -[1 (S)-[(tetrahydro-2(RS)-pyranyloxy)carbamoyl-4-phenyl-3-butenyl]-2'-isobutyl-4-methylvalerohydrazide used as the starting material was prepared as follows:

A solution of 0.459 g of (E)-2(R)-[1(S)-[(tetrahydro-2 (RS)-pyranyloxy)carbamoyl]-4-phenyl-3-butenyl]-2'-isobutyl-4-methylvalerohydrazide in 10 ml of dichloromethane was treated with 0.6 ml of pyridine and 0.85 g of 3-(dimethylamino)-1-propanesulphonyl chloride hydrochloride. The mixture was stirred overnight at room temperature. Evaporation gave a residue which was dissolved in ethyl acetate and washed with 5% aqueous sodium hydrogen carbonate and saturated aqueous sodium chloride. Drying over anhydrous magnesium sulphate and evaporation gave a residue which was purified by column chromatography on silica gel using methanol/dichloromethane (8:92) for the elution to give 0.184 g of (E)-2'-[3-(dimethylamino) propylsulphonyl]-2(R)-[1(S)-[1(tetrahydro-2(RS)-pyranyloxy)carbamoyl]-4-phenyl-3-butenyl]-2'-isobutyl-4-methylvalerohydrazide in the form of a gum.

MS: 609 (M+H)+.

EXAMPLE 8

(E)-2'-[3-(Diethylamino)propylsulphonyl]-2(R)-[1(S)-(hydroxycarbamoyl)-4-phenyl-3-butenyl]-2'-isobutyl-4-methylvalerohydrazide p-toluenesulphonate A solution of 0.16 g of (E)-2'-[3-(diethylamino) propylsulphonyl]-2(R)-[1(S)-[(tetrahydro-2(RS)-pyranyloxy)carbamoyl]-4-phenyl-3-butenyl]-2'-isobutyl-4-methylvalerohydrazide in 4 ml of methanol was treated with 0.057 g of p-toluenesulphonic acid monohydrate. The mixture was stirred for 2 hours at room temperature and evaporated. Trituration of the residue with diethyl ether gave 0.125 g of (E)-2'-[3-(diethylamino)propylsulphonyl]-2(R)-[1(S)-(hydroxycarbamoyl)-4-phenyl-3-butenyl]-2'-isobutyl-4-methylvalerohydrazide p-toluenesulphonate in the form of an off-white solid.

MS: 553 (M+H)+.

HPLC: Gradient elution using solvent A containing 5% solvent B increasing to 95% solvent B over 15 minutes; flow rate 1 ml/minute. Retention time: 11.46 minutes. Solvent A: $H_2O$/0.1% TFA; solvent B: $CH_3CN$/0.085% TFA. Column type: HYPERPEP 300A.

The (E)-2'-[3-(diethylamino)propylsulphonyl]-2(R)-[1 (S)-[(tetrahydro-2(RS)-pyranyloxy)carbamoyl]-4-phenyl-3-butenyl]-2'-isobutyl-4-methylvalerohydrazide used as the starting material was prepared as follows:

(i) A solution of 0.918 g of (E)-2(R)-[1(S)-[(tetrahydro-2 (RS)-pyranyloxy)carbamoyl]-4-phenyl-3-butenyl]-2'-isobutyl-4-methylvalerohydrazide in 10 ml of dichloromethane was treated with 0.202 ml of pyridine and 0.354 g of 3-chloropropanesulphonyl chloride. The mixture was stirred for 2 hours at room temperature. A further 0.177 g of 3-chloropropanesulphonyl chloride and 0.160 ml of pyridine were added and the mixture was stirred for a further 2 hours at room temperature. Evaporation gave a residue which was dissolved in ethyl acetate and washed in sequence with water, 5% aqueous citric acid, water, 5% aqueous sodium hydrogen carbonate and saturated aqueous sodium chloride. Drying over anhydrous magnesium sulphate, evaporation, and trituration with ether/hexane gave a residue which was purified by column chromatography on silica gel using hexane/ethyl acetate (6:4) for the elution, to give 0.8 g of (E)-2'-(3-chloropropylsulphonyl)-2(R)-[1(S)-[(tetrahydro-2 (RS)-pyranyloxy)carbamoyl]-4-phenyl-3-butenyl]-2'-isobutyl-4-methylvalerohydrazide in the form of a pale yellow solid.

MS: 600 (M+H)+.

(ii) A solution of 0.60 g of (E)-2'-(3-chloropropylsulphonyl)-2(R)-[1(S)-[(tetrahydro-2(RS)-pyranyloxy)carbamoyl]-4-phenyl-3-butenyl]-2'-isobutyl-4-methylvalerohydrazide in 10 ml of methyl ethyl ketone was treated with 0.18 g of sodium iodide and 1.04 ml of diethylamine. The mixture was heated at 80° C. for 4 hours and then at 60° C. for 48 hours. The mixture was diluted with ethyl acetate, washed with water and saturated aqueous sodium chloride, dried over anhydrous magnesium sulphate and evaporated. The residue was purified by column chromatography on silica gel using methanol/dichloromethane (1:9) for the elution to give 0.16 g of (E)-2'-[3-(diethylamino)propylsulphonyl]-2(R) -[1(S)-(tetrahydro-2(RS)-pyranyloxy)carbamoyl]-4-phenyl-3-butenyl]-2'-isobutyl-4-methylvalerohydrazide in the form of a gum.

MS: 637 (M+H)+.

EXAMPLE 9

2'-(3-Aminopropanesulphonyl)-2(R)-[1(S)-(hydroxycarbamoyl)-4-phenylbutyl]-2'-isobutyl-4-methylvalerohydrazide A solution of 0.15 g of (E)-2'-(3-aminopropanesulphonyl)-2(R)-[1(S)-(benzyloxycarbamoyl)-4-phenyl-3-butenyl]-2'-isobutyl-4-methylvalerohydrazide in 5 ml of methanol was hydrogenated in the presence of 60 mg of 10% palladium-on-charcoal until uptake of hydrogen was complete. The catalyst was removed by filtration and the solvent was evaporated. The residue was triturated with diethyl ether and there was obtained 0.088 g of 2'-(3-aminopropanesulphonyl)-2(R)-[1(S)-(hydroxycarbamoyl)-4-phenylbutyl]-2'-isobutyl-4-methylvalerohydrazide in the form of a pale pink solid.

MS: 499 (M+H)+.

HPLC: Gradient elution using solvent A containing 5% solvent B increasing to 95% solvent B over 15 minutes; flow rate 1 ml/minute. Retention time: 9.14 minutes. Solvent A: $H_2O$/0.1% TFA; solvent B: $CH_3CN$/0.085% TFA. Column type: HYPERPEP 300A.

The (E)-2'-(3-aminopropanesulphonyl)-2(R)-[1(S)-(benzyloxycarbamoyl)-4-phenyl-3-butenyl]-2'-isobutyl-4-methylvalerohydrazide used as the starting material was prepared as follows:

In a manner analogous to that described in Example 2 parts (i) and (ii), starting from (E)-2(R)-[1(S)-(benzyloxycarbamoyl)-4-phenyl-3-butenyl]-2'-isobutyl-4-methylvalerohydrazide and 3-phthalimidopropanesulphonyl chloride there was obtained (E)-2'-(3-aminopropanesulphonyl)-2(R)-[1(S)-(benzyloxycarbamoyl)-4-phenyl-3-butenyl]-2'-isobutyl-4-methylvalerohydrazide in the form of a white solid.

MS: 587 (M+H)+.

EXAMPLE 10

2'-[3-(Diethylamino)propylsulphonyl]-2(R)-[1(S)-(hydroxycarbamoyl)-4-phenylbutyl]-2'-isobutyl-4-methylvalerohydrazide In a manner analogous to that described in Example (9) from 0.28 g of (E)-2'-[3-(diethylamino)propylsulphonyl]-2(R)-[1(S)-(benzyloxycarbamoyl)-4-phenyl-3-butenyl]-2'-isobutyl-4-methylvalerhydrazide there was obtained 0.232 g of 2'-[3-(diethylamino)propylsulphonyl]-2(R)-[1(S)-(hydroxycarbamoyl)-4-phenylbutyl]-2'-isobutyl-4-methylvalerohydrazide in the form of an off-white solid.

MS: 555 (M+H)+.

HPLC: Gradient elution using solvent A containing 5% solvent B increasing to 95% solvent B over 15 minutes; flow rate I ml/minute. Retention time: 9.84 minutes. Solvent A: $H_2O$/0.1% TFA; solvent B: $CH_3CN$/0.085% TFA. Column type: HYPERPEP 300A.

The (E)-2'-[3-(diethylamino)propylsulphonyl]-2(R)-[1(S)-(benzyloxycarbamoyl)-4-phenyl-3-butenyl]-2'-isobutyl-4-methylvalerhydrazide used as the starting material was prepared as follows:

In a manner analogous to that described in Example 8, parts (i) and (ii), starting from (E)-2(R)-[1(S)-(benzyloxycarbamoyl)-4-phenyl-3-butenyl]-2'-isobutyl-4-methylvalerohydrazide and 3-chloropropanesulphonyl chloride there was obtained (E)-2'-[3-(diethylamino)propylsulphonyl]-2(R)-[(S)-(benzyloxycarbamoyl)-4-phenyl-3-butenyl]-2'-isobutyl-4-methylvalerohydrazide in the form of a gum.

MS: 643 (M+H)+.

EXAMPLE 11

2'-[3-(Dimethylamino)propylsulphonyl]-2(R)-[1(S)-(hydroxucarbamoyl)-4-phenylbutyl]-2'-isobutyl-4-methylvalerohydrazide.

In a manner analogous to that described in Example (9) from 0.17 g of (E)-2'-[3-(dimethylamino)propylsulphonyl]-2(R)-[1(S)-(benzyloxycarbamoyl)-4-phenyl-3-butenyl]-2'-isobutyl-4-methylvalerohydrazide there was obtained 0.089 g of 2'-[3-(dimethylamino)propylsulphonyl]-2(R)-[1(S)-(hydroxycarbamoyl)-4-phenylbutyl]-2'-isobutyl-4-methylvalerohydrazide in the form of a pink solid.

MS: 527 (M+H)+.

HPLC: Gradient elution using solvent A containing 5% solvent B increasing to 95% solvent B over 15 minutes; flow rate 1 ml/minute. Retention time: 9.41 minutes. Solvent A: $H_2O$/0.1% TFA; solvent B: $CH_3CN$/0.085% TFA. Column type: HYPERPEP 300A.

The (E)-2'-[3-(dimethylamino)propylsulphonyl]-2(R)-[1(S)-(benzyloxycarbamoyl)-4-phenyl-3-butenyl]-2'-isobutyl-4-methylvalerohydrazide used as the starting material was prepared as follows:

In a manner analogous to that described in Example 7 starting from (E)-[1(S)-(benzyloxycarbamoyl)-4-phenyl-3-butenyl]-2'-isobutyl-4-methylvalerohydrazide and 3-(dimethylamino)-1-propanesulphonyl chloride hydrochloride there was obtained (E)-2'-[3-(dimethylamino)propylsulphonyl]-2(R)-[1(S)-(benzyloxycarbonyl)-4-phenyl-3-butenyl]-2'-isobutyl-4-methylvalerohydrazide in the form of a gum.

MS: 615 (M+H)+.

BIBLIOGRAPHY

1. Soluble TNF Receptor (p75) fusion protein (Enbrel) as a therapy for rheumatoid arthritis. Moreland, L. W. Rheum. Dis. Clin. North Am. (1998) 24, p579–591.
2. The future role of anti-tumour necrosis factor alpha products in the treatment of Crohn's disease. Van Hogezand, R. A. and Verspaget, H. W. Drugs (1998) 56, p299–305.

(Note: numbers 3 and 4 not used.)

5. TNFalpha convertase enzyme from human arthritis-affected cartilage: Isolation of cDNA by differential display, expression of the active enzyme, and regulation of TNFalpha. J.Immunol (1998)160, p4570–4579. Patel, I. R., Attur,M. G., Patel, R. N., Stuchin, S. A., Abagyan, R. A., Abramson, S. B. and Amin,A. R.
6. Chondrocyte tumour necrosis factor receptors and focal loss of cartilage in osteoarthritis. Osteoarthritis Cartilage (1997) 5, p427–437. Webb, G. R., Westacott,C. J. and Elson, C. J.
7. Tumour necrosis factor alpha gene polymorphisms in chronic bronchitis. Am.J. Respiratory and Critical Care Medicine (1997),156, p1436–1439. Huang-Song-Lih, Su-Chern-Huey and Chang-Shi-Chuan.
8. Pathology of Asthma and COPD: A Synopsis. Eur. Resp. Rev. (1997) 7, p111–118. Jeffery, P. K.
9. Tumour necrosis factor alpha (TNFalpha)-induced ICAM-1 surface expression in airway epithelial cells in vitro: possible signal transduction mechanisms. Ann. N.Y. Acad. Sci (1996) 796, p30–37.
10. Investigational New Drugs, 1997, vol. 15, no. 1, p. 49–59 Journal of Molecular Medicine (Berlin), 1995, vol. 73, no. 7, p. 333–346
11. Association between tumour necrosis factor in serum and cachexia in patients with prostate cancer. Clin Cancer Res. (1998), 4, pp1743–1748. Nakashima, J., Tachibara, M., Ueno, M., Miyajima, A., Baba,S. and Murai, M.
12. Effect of FRI 43430, a Novel Cytokine Suppressive Agent, on Adenocarcinoma Colon 26-Induced Cachexia in Mice. Anticancer Res. (1998) 18, pp139–144. Yamoto, N., Kawamura, I., Nishigaki, F., Tsujimoto, S., Naoe, Y., Inami, M., Elizabeth, L., Manda, T. and Shimomura, K.
13. Tumour necrosis factor in congestive heart failure: a mechanism of disease for the new millenium. Ceconi, C., Curello, S., Bachetti, T., Corti, A. and Ferrari, R. Prog. Cardiovasc. Dis. (1998) 48, pp25–30.
14. Cardiac failure in transgenic mice with myocardial expression of tumour necrosis factor-alpha. Circulation (1998) 97, pp1375–1381. Bryant, D., Becker, L., Richardson, J., Shelton, J., Franco.F., Peshock, R., Thompson, M. and Giroir, B.
15. Journal of the American Academy of Dermatology, 1996, vol. 35, no. 6, p. 969–979.
16. Peripheral blood monocytes in psoriatic patients overproduce cytokines. J. Derm. Sci. (1998),17, p223–232. Okubo, Y and Koga, M.
17. Mast cells of psoriatic and atopic dermatitis skin are positive for TNFalpha and their degranulation is associated with expression of ICAM-1 in the epidermis. Archives of Dermatological Research (1998),290, p353–359. Ackermann, L. and Harvima, I. T.
18. Cytokine-induced fever in obese(fa/fa) and lean(Fa/Fa) Zucker rats. Am. J. Physiol. Regul. Integr. Comp. Physiol. (1998) 275, R1353–1357. Plata-Salaman, C. R., Peloso, E. and Satinoff, E.
19. Levels of tumour necrosis factor and soluble TNF receptors during malaria fever episodes in the community. Trans. R. Soc. Trop. Med. Hyg. (1998) 92, pp50–53. McGuire, W., Alessandro, U., Stephens, S., Olaleye, B. O., Langerock, P., Greenwood, B. M. and Kwiatkowski, D.
20. Tumour necrosis factor-alpha as a target of melanocortin in haemorrhagic shock, in the anaesthetised rat. British J. Pharmacol. (1998) 124, pp1587–1590. Altavilla, D., Cainazzo, M. M., Squadrito, F., Guarini, S., Bertolini, A. and Bazzani, C.
21. Significance of TNF in haemorrhage-related haemodynamic alterations, organ injury and mortality in rats. Bahrami, S., Yao, Y.M., Leichtfried, G., Redl, H., Marzi, I. And Schlag, G. Am.J.Physiol. Heart. Circ. Physiol. (1997), 272, pp41–45.
22. Pentoxifylline reduces plasma tumour necrosis factor alpha concentration in premature infants with sepsis. Eur. J. Pediatrics (1996) 155, pp404–409. Lauterbach, R. and Zembala, M.

What is claimed is:

1. A hydrazine derivative, being a compound of the formula

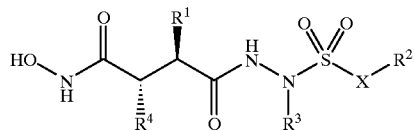

(I)

wherein
$R^1$ is lower alkyl, lower alkenyl, lower cycloalkyl, lower cycloalkyl-lower alkyl, aryl or aryl-lower alkyl;
$R^2$ is heterocyclyl or $NR^5R^6$;
$R^3$ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
$R^4$ is lower alkyl, lower alkenyl, lower cycloalkyl, lower cycloalkyl-lower alkyl, -Z-aryl, -Z-heterocyclyl or $—(CH_2)_n—CH=CR^7R^8$;
$R^5$ and $R^6$ are each independently hydrogen or lower alkyl;
$R^7$ and $R^8$ are each independently hydrogen or lower alkyl, or $R^7$ and $R^8$ together are lower alkylene or lower alkylene in which one $CH_2$ group is replaced by S, O, or $N(R^{11})$ wherein $R^{11}$ is hydrogen or lower alkyl;
X is $—(CH_2)_{1-5}—$ or $—(CH_2)_l—Y—(CH_2)_m—$ in which l and m are each independently 0, 1 or 2 and Y is arylene, lower cycloalkylene or heterocyclylene;

Z is $—(CH_2)_p—W—(CH_2)_q—$ in which p and q are each independently 0, 1, 2 or 3 and W is absent or is $—CH=CH—$, $—C\equiv C—$, $—S—$, $—O—$, $—NH—$, $—NHCO—$, $—CONH—$, $—SO_2—$, $—NHSO_2—$, $—SO_2NH—$, $—NHCONH—$ or $—NHSO_2NH—$;
n is 0, 1 or 2;
wherein each heterocyclyl or heteroaryl is independently unsubstituted or substituted by halogen, lower alkyl, lower alkoxy, or oxo;
or a mixture containing said compound and one or more optical isomers thereof, or a pharmaceutically acceptable salt of said compound or said mixture.

2. The hydrazine derivative according to claim 1, wherein $R^1$ is lower alkyl.

3. The hydrazine derivative according to claim 2, wherein $R^1$ is isobutyl.

4. The hydrazine derivative according to of claim 1, wherein $R^2$ is pyridyl.

5. The hydrazine derivative according to claim 4, wherein $R^2$ is 2-pyridyl.

6. The hydrazine derivative according to claim 1, wherein $R^2$ is $NR^5R^6$ in which $R^5$ and $R^6$ are the same and are selected from the group consisting of hydrogen, methyl, and ethyl.

7. The hydrazine derivative according to claim 1, wherein $R^2$ is morpholinyl.

8. The hydrazine derivative according to claim 1, wherein $R^3$ is lower alkyl.

9. The hydrazine derivative according to claim 8, wherein $R^3$ is isobutyl.

10. The hydrazine derivative according to claim 1, wherein $R^4$ is —Z-aryl.

11. The hydrazine derivative according to claim 10, wherein Z is $—(CH_2)_2—$ or $—CH_2CH=CH—$ and said aryl is unsubstituted phenyl.

12. The hydrazine derivative according to claim 1 wherein X is $—(CH_2)_{1-4}—$ or $—CH_2—Y—$ in which Y is arylene.

13. The hydrazine derivative according to claim 12, wherein Y is phenylene.

14. The hydrazine derivative according to claim 13, wherein Y is o-phenylene.

15. The hydrazine derivative according to claim 1, (E)-2'-(2-Aminoethanesulphonyl)-2(R)-[1(S)-(hydroxycarbamoyl)-4-phenyl-3-butenyl]-2'-isobutyl-4-methylvalerohydrazide or a pharmaceutically acceptable salt thereof.

16. The hydrazine derivative according to claim 1, 2'-(2-aminobenzenesulphonyl)-2(R)-[1(S)-(hydroxycarbamoyl)-4-phenylbutyl]-2'-isobutyl-4-methylvalerohydrazide or a pharmaceutically acceptable salt thereof.

17. The hydrazine derivative according to claim 1, (E)-2'-[3-(diethylamino)propylsulphonyl]-2(R)-[1(S)-(hydroxycarbamoyl)-4-phenyl-3-butenyl]-2'-isobutyl-4-methylvalerohydrazide or a pharmaceutically acceptable salt thereof.

18. The hydrazine derivative according to claim 1, (E)-2'-(3-aminopropanesulphonyl))-2(R)-[1(S)-(hydroxycarbamoyl)-4-phenyl-3-butenyl]-2'-isobutyl-4-methylvalerohydrazide or a pharmaceutically acceptable salt thereof.

19. The hydrazine derivative according to claim 1, (E)-2(R)-[1(S)-(hydroxycarbamoyl)-4-phenyl-3-butenyl]-2'-isobutyl-4-methyl-2'-[2-(2-pyridyl)ethanesulphonyl]valerohydrazide or a pharmaceutically acceptable salt thereof.

20. The hydrazine derivative according to claim 1, (E)-2(R)-[1(S)-(hydroxycarbamoyl)-4-phenyl-3-butenyl]-2'-isobutyl-4-methyl-2'-(3-morpholinopropylsulphonyl)valerohydrazide or a pharmaceutically acceptable salt thereof.

21. The hydrazine derivative according to claim 1, (E)-2(R)-[1(S)-(hydroxycarbamoyl)-4-phenyl-3-butenyl]-2'- isobutyl-4-methyl-2'-3-(dimethylamino)propylsulphonyl] valerohydrazide or a pharmaceutically acceptable salt thereof.

22. The hydrazine derivative according to claim 1, (E)-2'-(4-Aminobutanesulphonyl)-2(R)-[1(S)-(hydroxycarbamoyl)-4-phenyl-3-butenyl]-2'-isobutyl-4-methylvalerohydrazide or a pharmaceutically acceptable salt thereof.

23. A process for producing a hydrazine derivative of the formula

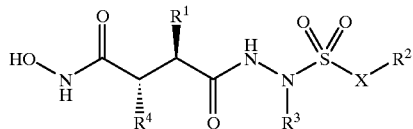

(I)

wherein
R$^1$ is lower alkyl, lower alkenyl, lower cycloalkyl, lower cycloalkyl-lower alkyl, aryl or aryl-lower alkyl;
R$^2$ is heterocyclyl or NR$^5$R$^6$;
R$^3$ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
R$^4$ is lower alkyl, lower alkenyl, lower cycloalkyl, lower cycloalkyl-lower alkyl, —Z-aryl, —Z-heterocyclyl or —(CH$_2$)n—CH=CR$^7$R$^8$;
R$^5$ and R$^6$ are each independently hydrogen or lower alkyl;
R$^7$ and R$^8$ are each independently hydrogen or lower alkyl, or R$^7$ and R$^8$ together are lower alkylene or lower alkylene in which one CH$_2$ group is replaced by S, O, or N(R$^{11}$) wherein R$^{11}$ is hydrogen or lower alkyl;
X is —(CH$_2$)$_{1-5}$— or —(CH$_2$)$_l$—Y—(CH$_2$)$_m$— in which l and m are each 0, 1 or 2 and Y is arylene, lower cycloalkylene or heterocyclylene;
Z is —(CH$_2$)$_p$—W—(CH$_2$)$_q$— in which p and q are each 0, 1, 2 or 3 and W is absent or is —CH=CH—, —C≡C—, —S—, —O—, —NH—, —NHCO—, —CONH—, —SO$_2$—, —NHSO$_2$—, —SO$_2$NH—, —NHCONH— or —NHSO$_2$NH—;
n is 0, 1 or 2;
wherein each heterocyclyl or heteroaryl is independently unsubstituted or substituted by halogen, lower alkyl, lower alkoxy, or oxo;
which process comprises
cleaving off the protecting group R$^9$ from a compound of the formula

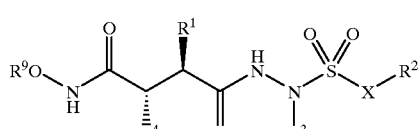

(II)

wherein R$^9$ is a hydroxy protecting group.

24. The process of claim 23, further comprising converting the hydrazine derivative into a pharmaceutically acceptable salt thereof.

25. A process for producing a hydrazine derivative of the formula

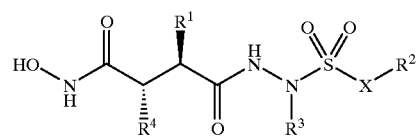

(I)

wherein
R$^1$ is lower alkyl, lower alkenyl, lower cycloalkyl, lower cycloalkyl-lower alkyl, aryl or aryl-lower alkyl;
R$^2$ is amino;
R$^3$ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
R$^4$ is —CH$_2$CH$_2$CH$_2$-aryl;
X is —CH$_2$-arylene;
Z is —(CH$_2$)$_p$—W—(CH$_2$)$_q$— in which p and q are each independently 0, 1, 2 or 3 and W is absent or is —CH=CH—, —C≡C—, —S—, —O—, —NH—, —NHCO—, —CONH—, —SO$_2$—, —NHSO$_2$—, —SO$_2$NH—, —NHCONH— or —NHSO$_2$NH—;
n is 0, 1 or 2;
wherein each heterocyclyl or heteroaryl is independently unsubstituted or substituted by halogen, lower alkyl, lower alkoxy, or oxo;

which process comprises cleaving off the protecting group R$^9$ from a compound of the formula

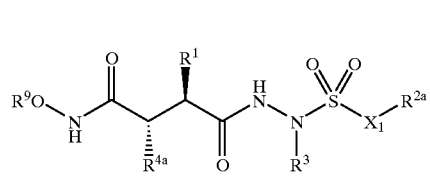

(III)

wherein R$^{4a}$ is —CH$_2$CH=CH-aryl, X$_1$ is —CH$_2$-arylene, R$^{2a}$ is nitro and R$^9$ is a hydroxy protecting group, and reducing the resulting compound of the formula

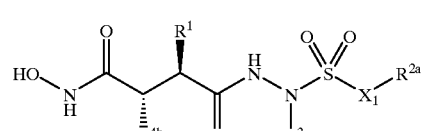

(IV)

wherein R$^4$bis —CH$_2$CH$_2$CH$_2$-aryl.

26. The process of claim 25, further comprising converting the hydrazine derivative into a pharmaceutically acceptable salt thereof.

27. A compound of the formula

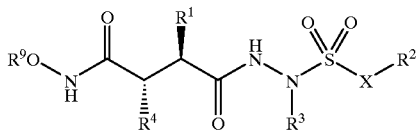

(II)

wherein
R¹ is lower alkyl, lower alkenyl, lower cycloalkyl, lower cycloalkyl-lower alkyl, aryl or aryl-lower alkyl;
R² is heterocyclyl or NR⁵R⁶;
R³ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
R⁴ is lower alkyl, lower alkenyl, lower cycloalkyl, lower cycloalkyl-lower alkyl, —Z-aryl, —Z-heterocyclyl or —(CH₂)$_n$—CH═CR⁷R⁸;
R⁵ and R⁶ are each independently hydrogen or lower alkyl;
R⁷ and R⁸ are each independently hydrogen or lower alkyl, or R⁷ and R⁸ together are lower alkylene or lower alkylene in which one CH₂ group is replaced by S, O, or N(R¹¹) wherein R¹¹ is hydrogen or lower alkyl;
R⁹ is a hydroxy protecting group;
X is —(CH₂)$_{1-5}$— or —(CH₂)$_l$—Y—(CH₂)$_m$— in which l and m are each independently 0, 1 or 2 and Y is arylene, lower cycloalkylene or heterocyclylene;
Z is —(CH₂)$_p$—W—(CH₂)$_q$— in which p and q each independently or 0, 1, 2 or 3 and W is absent or is —CH═CH—, —C≡C—, —S—, —O—, —NH—, —NHCO—, —CONH—, —SO₂—, —NHSO₂—, —SO₂NH—, —NHCONH— or —NHSO₂NH—;
n is 0, 1 or 2;
wherein each heterocyclyl or heteroaryl is independently unsubstituted or substituted by halogen, lower alkyl, lower alkoxy, or oxo;
or a mixture containing said compound and one or more optical isomers thereof, or a pharmaceutically acceptable salt of said compound or said mixture.

28. A compound of the formula

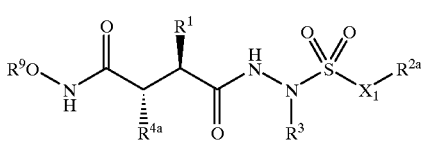

(III)

wherein
R¹ is lower alkyl, lower alkenyl, lower cycloalkyl, lower cycloalkyl-lower alkyl, aryl or aryl-lower alkyl;
R²$^a$ is nitro;
R³ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
R⁴$^a$ is —CH₂CH═CH-aryl;
R⁵ and R⁶ are each independently hydrogen or lower alkyl;
R⁷ and R⁸ are each independently hydrogen or lower alky, or R⁷ and R⁸ together are lower alkylene or lower alkylene in which one CH₂ group is replaced by S, O, or N(R¹¹) wherein R¹¹ is hydrogen or lower alkyl;
R⁹ is a hydroxy protecting group;
X₁ is —CH₂-arylene;
Z is —(CH₂)$_p$—W—(CH₂)$_q$— in which p and q are each independently 0, 1, 2 or 3 and W is absent or is —CH═CH—, —C≡C—, —S—, —O—, —NH—, —NHCO—, —CONH—, —SO₂—, —NHSO₂—, —SO₂NH—, —NHCONH— or —NHSO₂NH—;
n is 0, 1 or 2;
wherein each heterocyclyl or heteroaryl is independently unsubstituted or substituted by halogen, lower alkyl, lower alkoxy, or oxo;
or a mixture containing said compound and one or more optical isomers thereof, or a pharmaceutically acceptable salt of said compound or said mixture.

29. A compound of the formula

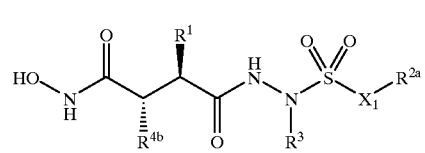

(IV)

wherein
R¹ is lower alkyl, lower alkenyl, lower cycloalkyl, lower cycloalkyl-lower alkyl, aryl or aryl-lower alkyl;
R²$^a$ is nitro;
R³ is hydrogen, lower alkyl, halo-lower alkyl, cyano-lower alkyl, hydroxy-lower alkyl, amino-lower alkyl, lower alkoxy-lower alkyl, lower alkoxycarbonyl-lower alkyl, lower cycloalkyl-lower alkyl, aryl-lower alkyl, heterocyclyl-lower alkyl, heterocyclylcarbonyl-lower alkyl, lower alkenyl, lower alkynyl, lower cycloalkyl, aryl, heteroaryl or aryl-lower alkyl;
R⁴$^b$ is CH₂CH₂CH₂-aryl;
X₁ is —CH₂-arylene;
Z is —(CH₂)$_p$—W—(CH₂)$_q$— in which p and q are each independently 0, 1, 2 or 3 and W is absent or is —CH═CH—, —C≡C—, —S—, —O—, —NH—, —NHCO—, —CONH—, —SO₂—, —NHSO₂—, —SO₂NH—, —NHCONH— or —NHSO₂NH—;
n is 0, 1 or 2;
wherein each heterocyclyl or heteroaryl is independently unsubstituted or substituted by halogen, lower alkyl, lower alkoxy, or oxo;
or a mixture containing said compound and one or more optical isomers thereof, or a pharmaceutically acceptable salt of said compound or said mixture.

* * * * *